(12) United States Patent
Lifsches (10) Patent No.: US 12,135,725 B2
(45) Date of Patent: *Nov. 5, 2024

(54) EFFICIENT SIMILARITY SEARCH

(71) Applicant: GSI Technology Inc., Sunnyvale, CA (US)

(72) Inventor: Samuel Lifsches, Tel Aviv (IL)

(73) Assignee: GSI Technology Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/311,938

(22) Filed: May 4, 2023

(65) Prior Publication Data

US 2023/0273933 A1    Aug. 31, 2023

Related U.S. Application Data

(63) Continuation of application No. 16/923,127, filed on Jul. 8, 2020, now Pat. No. 11,645,292.

(60) Provisional application No. 63/043,821, filed on Jun. 25, 2020, provisional application No. 62/990,513, filed on Mar. 17, 2020.

(51) Int. Cl.
| | | |
|---|---|---|
| *G06F 16/24* | (2019.01) | |
| *G06F 16/22* | (2019.01) | |
| *G06F 16/2455* | (2019.01) | |
| *G06F 16/2458* | (2019.01) | |
| *G06F 18/23213* | (2023.01) | |
| *G06F 18/2413* | (2023.01) | |
| *H03M 13/15* | (2006.01) | |
| *H03M 13/29* | (2006.01) | |

(52) U.S. Cl.
CPC ...... *G06F 16/2468* (2019.01); *G06F 16/2237* (2019.01); *G06F 16/24558* (2019.01); *G06F 18/23213* (2023.01); *G06F 18/24147* (2023.01); *H03M 13/1575* (2013.01); *H03M 13/2942* (2013.01)

(58) Field of Classification Search
CPC ........... G06F 16/2468; G06F 16/24558; G06F 16/2237
See application file for complete search history.

(56) References Cited

U.S. PATENT DOCUMENTS

| | | | | |
|---|---|---|---|---|
| 8,238,173 | B2* | 8/2012 | Akerib | G11C 7/1006 |
| | | | | 365/191 |
| 9,238,173 | B2* | 1/2016 | Ohta | G06F 3/038 |
| 9,859,005 | B2* | 1/2018 | Akerib | G11C 15/046 |
| 10,153,042 | B2* | 12/2018 | Ehrman | G11C 15/04 |
| 11,645,292 | B2 | 5/2023 | Lifsches | |
| 2018/0081566 | A1* | 3/2018 | Liu | G06F 3/064 |

* cited by examiner

*Primary Examiner* — Baoquoc N To
(74) *Attorney, Agent, or Firm* — Heidi Brun Associates Ltd.

(57) ABSTRACT

A system for measuring similarity between a binary query vector and a plurality of binary candidate vectors includes a storage unit and a processor. The storage unit stores the binary query vector and the plurality of candidate vectors, and the processor performs Tanimoto calculations in terms of Hamming distances.

8 Claims, 9 Drawing Sheets

EFFICIENT SIMILARITY SEARCH

CROSS REFERENCE TO RELATED APPLICATIONS

This application is a continuation application of U.S. patent application Ser. No. 16/923,127, filed Jul. 8, 2020, which claims priority from U.S. Provisional Patent Application 62/990,513 filed Mar. 17, 2020 and U.S. Provisional Patent Application 63/043,821 filed Jun. 25, 2020 which are incorporated herein by reference.

FIELD OF THE INVENTION

The present invention relates to search in general and to an efficient method for similarity search in particular.

BACKGROUND OF THE INVENTION

Similarity searches are used to find items that are similar to one another. For example, chemists use such tools to search chemoinformatics and bioinformatics databases to help in the design of new molecules. The underlying assumption in these computational methods is that molecules that are structurally similar are likely to have similar biological and physicochemical properties. This is commonly called the 'similarity principle.'

There are five main search methods utilized in molecular searches of databases: text search, molecular formula search, identity search, substructure search and similarity search.

Text search is simple keyword searching, for example for the word 'aspirin.'

Molecular formula search is used to find molecules that contain a certain number and type of elements, for example C6H6.

Identity search is used to locate a specific chemical structure that is "identical" to a query structure.

Substructure search requires a specialized search engine that identifies illustrations of molecules to find a chemical structure that occurs as a part of a bigger chemical structure.

Similarity search is used to find molecules that are similar to a query molecule. The aspects of the molecule used in the comparison may vary depending on the application. The quantity of similar aspects may also change depending on the nature of the search.

Similarity searches operate on similarity measures. All similarity measures comprise three basic components—molecular descriptor, weight, and similarity coefficient.

A molecular descriptor may also be called a feature. A feature is a digital representation of a molecule's physical, chemical or other characteristic. A group of features is called a 'molecular fingerprint.'

Weight is used to prioritize and deprioritize the features to reflect their relative importance in a particular fingerprint method. Over time, different molecular fingerprint methods have been developed to address different measurement needs. They may contain a different number and type of features and weightings, obtained in different ways.

The similarity coefficient, also called the similarity metric, provides a numeric value to the degree of similarity between two molecules. The molecular fingerprint type being used, the search sample size and other factors may influence the selection of the similarity metric. Examples of similarity metrics are Tanimoto, Hamming, L1, L2 and Jaccard.

Chemists and biologists often use the Tanimoto metric $\alpha$ to quantify similarity between molecular fingerprints. The Tanimoto metric $\alpha$ is the ratio of the features that are common to both of the molecular fingerprints being compared (i.e. the intersection of their fingerprint features) and the features that are present in both molecules together (i.e. the union of their fingerprint features) and can be represented by:

$$\alpha(A, B) = \frac{|A \cap B|}{|A \cup B|} = \frac{|A \cap B|}{|A| + |B| - |A \cap B|} \quad (1)$$

where A and B are molecular fingerprints of molecules a and b respectively, $\cap$ is the intersection of the fingerprint features and $\cup$ is the union of the fingerprint features, and where the value of $\alpha(A,B)$ is between zero and one—the more similar the molecular fingerprints A and B, the more the value of the Tanimoto metric $\alpha(A,B)$ tends to 1.

For example, if a molecule a has 28 features and a molecule b has 32 features of which 15 of the features are common to both a and b, then the Tanimoto metric $\alpha$ can be calculated using equation 1 thusly:

$$\alpha(A, B) = \frac{15}{28 + 32 - 15} = \frac{1}{3} = 0.33$$

Figure 1:
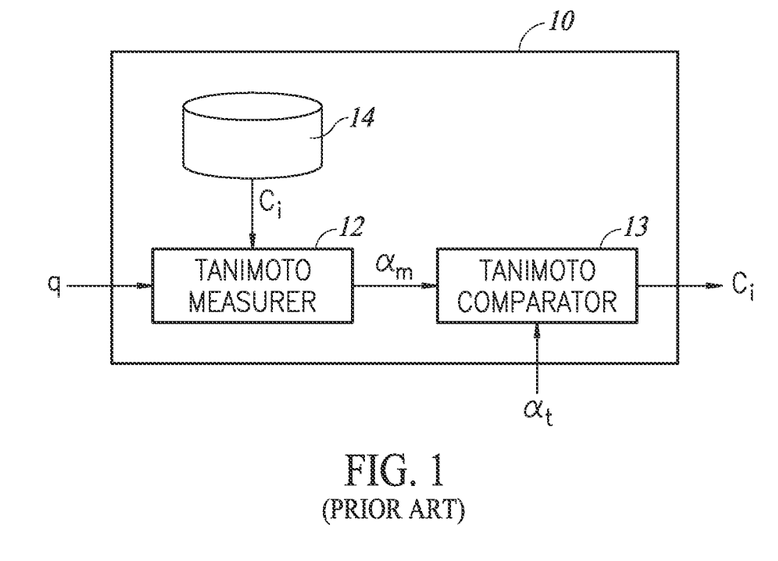
FIG. 1 is a schematic illustration of a prior art Tanimoto measurement system.

Reference is now made to FIG. 1 which illustrates a prior art Tanimoto measurement system 10 comprising a Tanimoto measurer 12, a Tanimoto comparator 13 and a candidate vector database 14. Tanimoto measurer 12 measures the Tanimoto metric $\alpha_m$ between a query vector q and a candidate vector C from candidate vector database 14. Tanimoto comparator 13 then compares the measured Tanimoto metric $\alpha_m$ to a defined threshold Tanimoto metric $\alpha_t$. Threshold Tanimoto metric at defines the value of $\alpha_m$ above which the compared vectors are deemed similar. For the above-mentioned example, if $\alpha_t$ is defined as 0.85, then the measured Tanimoto metric am of 0.33 indicates that q and C are not similar. If $\alpha_m$ is equal to or greater than $\alpha_t$, Tanimoto comparator 13 identifies vector C as a valid candidate vector. This measurement is repeated for all vectors in candidate vector database 14.

As molecular fingerprints may contain many thousands of features, and molecular fingerprint databases can contain hundreds of thousands of candidates, a similarity search of the molecular fingerprints using the Tanimoto metric may be computationally expensive, complex, and time-consuming.

SUMMARY OF THE PRESENT INVENTION

There is therefore provided, in accordance with a preferred embodiment of the present invention, a system for measuring similarity between a binary query vector and a plurality of binary candidate vectors. The system includes a storage unit and a processor. The storage unit stores the binary query vector and the plurality of candidate vectors, and the processor performs Tanimoto calculations in terms of Hamming distances. The processor includes a Tanimoto to Hamming threshold converter, a Hamming measurer, and a Hamming comparator. The Tanimoto to Hamming threshold converter converts a Tanimoto threshold into a Hamming threshold. The Hamming measurer measures the Hamming distances between the candidate vectors and the query vector. The Hamming comparator selects candidate vectors whose Hamming distance from the query vector is less than or equal to the Hamming threshold.

Additionally, in accordance with a preferred embodiment of the present invention, the Tanimoto threshold and the Hamming distance are a function of pop counts, and Boolean XOR functions between the candidate vector and the query vector.

Further, in accordance with a preferred embodiment of the present invention, the Tanimoto to Hamming threshold converter includes a pop counter and a Hamming threshold calculator. The pop counter counts the number of occurrences of a selected symbol in one of the binary vectors. The Hamming threshold calculator calculates the Hamming threshold from the Tanimoto metric from pop counts of the query and one of the candidate vectors.

Still further, in accordance with a preferred embodiment of the present invention, the Hamming measurer includes an XOR calculator and a pop counter. The XOR calculator calculates a XOR between two the binary vectors, and the pop counter counts the number of occurrences of a logical true value in the output of the XOR calculator.

Moreover, in accordance with a preferred embodiment of the present invention, the system also includes a chunker and a chunk comparator. The chunker groups the candidate vectors according to their pop counts into chunks. The chunk comparator rejects those the chunks which cannot contain the candidate vectors similar to the query vector and provides the non-rejected chunks to the Hamming measurer.

Further, in accordance with a preferred embodiment of the present invention, the chunker includes a pop counter and a vector sorter. The pop counter counts the pop count of the candidate vectors and the vector sorter groups the candidate vectors into chunks with homogeneous pop counts.

Still further, in accordance with a preferred embodiment of the present invention, the chunk comparator includes a pop counter and a Hamming minimum comparator. The pop counter counts the pop count of the chunks. The Hamming minimum comparator compares the pop count of the chunks with the Hamming threshold and rejects the chunks that have a pop count higher than the Hamming threshold.

Additionally, in accordance with a preferred embodiment of the present invention, the system includes a clusterer and a cluster comparator. The clusterer groups the candidate vectors in the chunks into clusters with prototypical centroids by means of a clustering algorithm, and the cluster comparator selects clusters with the centroid similar to the query vector.

Moreover, in accordance with a preferred embodiment of the present invention, the clustering algorithm is a K-means algorithm or a K nearest neighbor algorithm.

Still further, in accordance with a preferred embodiment of the present invention, the cluster comparator includes a Hamming measurer and a Hamming comparator. The Hamming measurer measures the Hamming distance between the query vector and the centroid. The Hamming comparator selects only the clusters with the centroid within the Hamming measurement threshold of the query vector and the clusters.

Additionally, in accordance with a preferred embodiment of the present invention, the system is implemented in associative memory.

There is also provided, in accordance with a preferred embodiment of the present invention a method for measuring similarity between a binary query vector and a plurality of binary candidate vectors. The method includes storing the binary query vector and the plurality of candidate vectors, executing Tanimoto metric calculations in terms of Hamming distances, and converting a Tanimoto threshold to a Hamming threshold. The method also includes measuring Hamming distances between the candidate vectors and the query vector, and selecting candidate vectors whose Hamming distance from the query vector is less than or equal to the Hamming threshold.

Moreover, in accordance with a preferred embodiment of the present invention, converting includes counting the number of occurrences of a selected symbol in one of the binary vectors, and calculating the Hamming threshold from the Tanimoto metric from pop counts of the query and one of the candidate vectors.

Further, in accordance with a preferred embodiment of the present invention, measuring includes calculating a XOR between two the binary vectors, and counting the number of occurrences of a logical true value in the output of the calculating.

Still further, in accordance with a preferred embodiment of the present invention, the method also includes chunking the candidate vectors according to their pop counts into chunks, and rejecting those the chunks which cannot contain the candidate vectors similar to the query vector and providing the non-rejected chunks for measuring.

Additionally, in accordance with a preferred embodiment of the present invention, chunking includes counting the pop count of the candidate vectors, and sorting, to group the candidate vectors into chunks with homogeneous pop counts.

Moreover, in accordance with a preferred embodiment of the present invention, rejecting includes counting the pop count of the chunks, and comparing the pop count of the chunks with the Hamming threshold and rejecting the chunks with pop count higher than the Hamming threshold.

Further, in accordance with a preferred embodiment of the present invention, the method also includes clustering the candidate vectors in the chunks into clusters with prototypical centroids by means of a clustering algorithm, and selecting clusters with the centroid similar to the query vector.

Additionally, in accordance with a preferred embodiment of the present invention, selecting includes measuring the Hamming distance between the query vector and the centroid, and choosing only the clusters with the centroid within the Hamming measurement threshold of the query vector and the chunk.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Applicant has realized that Tanimoto metric $\alpha$ may be calculated in terms of another similarity search metric, Hamming distance h, and that Hamming distance h may be calculated with simple Boolean operations. As a result, molecular search may be significantly sped up, typically by orders of magnitude.

Figure 2A:
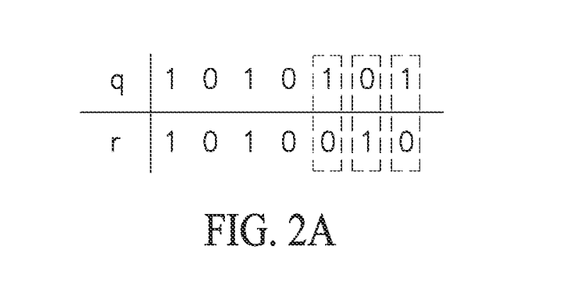
FIGS. 2A and 2B are pictorial illustrations of binary vectors.

Applicant has realized, as detailed herein below, that by clustering candidate vectors C in advance, such as by a k-means algorithm, a plurality of candidate vectors C can be rejected as dissimilar before having been measured. However, clustering with k-means is difficult with the Tanimoto metric $\alpha$. Applicant has realized that finding cluster centroids for k-means using Hamming distance h is a simple Boolean operation. Hamming distance h between two binary vectors of the same length is defined as the number of corresponding bit positions at which the symbols are different. Reference is now made to FIG. 2A which illustrates two binary vectors q and r. Binary vector q has a length of 7 bits and a value 1010101. Binary vector r also has a length of 7 bits but has a value of 1010010. It can be seen that the 3 least significant bit positions of vector q and vector r contain symbols that are different. Vector q contains symbols 101 while vector r contains symbols 010. All other bit positions contain similar symbols. Here the Hamming distance h between vector q and vector r is h(q,r)=3. So, the bit positions that contribute to the total Hamming distance are those with dissimilar symbols in corresponding bit positions. If the symbols, in this case either a 1 or a 0, are in both corresponding bit positions, then they have no impact on the Hamming distance.

It will be appreciated that Boolean operator XOR is defined as an operator whose output is logically true when only one of two inputs to it are logically true, but not when both inputs are logically true or logically false. This is the same logic as we applied to the corresponding bits in vector q and vector r: If the symbols differed, they added to the Hamming distance h (like a logical true) and if they were similar, they did not affect the Hamming distance h (like a logical false).

Figure 2B:
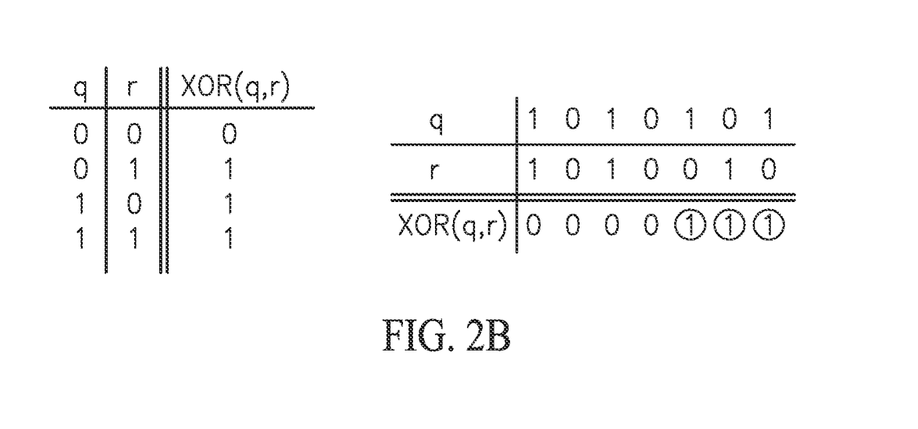

Reference is now made to FIG. 2B which illustrates the Boolean XOR function and the XOR of vector q and vector r. Boolean operator XOR is defined as an operator whose output is logically true when only one of two inputs to it are logically true, but not when both inputs are logically true or logically false. Hamming distance h is the count of the number of corresponding bits where the symbols, or in this case bits, differ. The Boolean function that counts the occurrence of logical trues, in our case 1s, in a binary vector is called a pop count. So Hamming distance h can be defined as the pop count of the XOR of vector q and vector r. This can be represented by:

$$h(q,r) = \text{pop}(\text{XOR}(q,r)) \qquad (2)$$

where pop is a pop count, and XOR(q,r) is the XOR of vector and vector r.

Tanimoto coefficient $\alpha$ may be expressed in terms of Hamming distance h and pop counts of two vectors, vector A and vector B as follows:

$$\alpha(A, B) = \frac{\text{pop}(A) + \text{pop}(B) - h(A, B)}{\text{pop}(A) + \text{pop}(B) + h(A, B)} \qquad (3)$$

where $\alpha(A,B)$ is the Tanimoto coefficient between vector A and vector B, pop(A) and pop(B) are the pop counts of binary vectors A and B, respectively, and h(A,B) is the Hamming distance between vector A and vector B as defined in equation 2.

It should be noted that Hamming distance is a 'dissimilarity' metric, which means that as two compared vectors become more similar to one another, then the value of the Hamming distance h between them tends 1 to 0. Conversely, as Tanimoto coefficient is a similarity metric, so as two compared vectors become more similar to one another, then the value of the Tanimoto coefficient tends from 0 to 1.

Applicant has realized that pop count and XOR are two very simple Boolean operations which may be easily calculated.

In practice, when chemists and biologists make similarity measurements, they may compare the results with a threshold value. The threshold value, for example when using Tanimoto coefficient, may be chosen based on many factors such as sample set size and number of features. It will be appreciated that as Tanimoto $\alpha_m$ can be measured between two binary vectors in terms of measured Hamming distance $h_m$, then Tanimoto threshold $\alpha_t$, which is the value of $\alpha_m$ above which two binary vectors are deemed to be similar, can be defined in terms of Hamming threshold $h_t$, which is the threshold below which two binary vectors are deemed to be similar.

By rearranging the terms in equation 3, Hamming threshold $h_t$ can be expressed as follows:

$$h_t(A, B) = (\text{pop}(A) + \text{pop}(B)) \times \left(\frac{1 - \alpha_t(A, B)}{1 + \alpha_t(A, B)}\right) \quad (4)$$

where $h_t(A, B)$ is the calculated Hamming threshold value for Hamming distance $h_m$ measured between two vectors, vector A and vector B, and $\alpha_t(A, B)$ is the predefined Tanimoto threshold $\alpha_t$ for Tanimoto coefficient $\alpha_m$ measured between the same two vectors, vector A and vector B.

Thus, as Applicant has realized, Tanimoto metric $\alpha$ can be calculated in terms of Hamming distance h and Boolean pop counts, and that Hamming distance h itself can be calculated in terms of Boolean XOR and pop counts.

Figure 3:
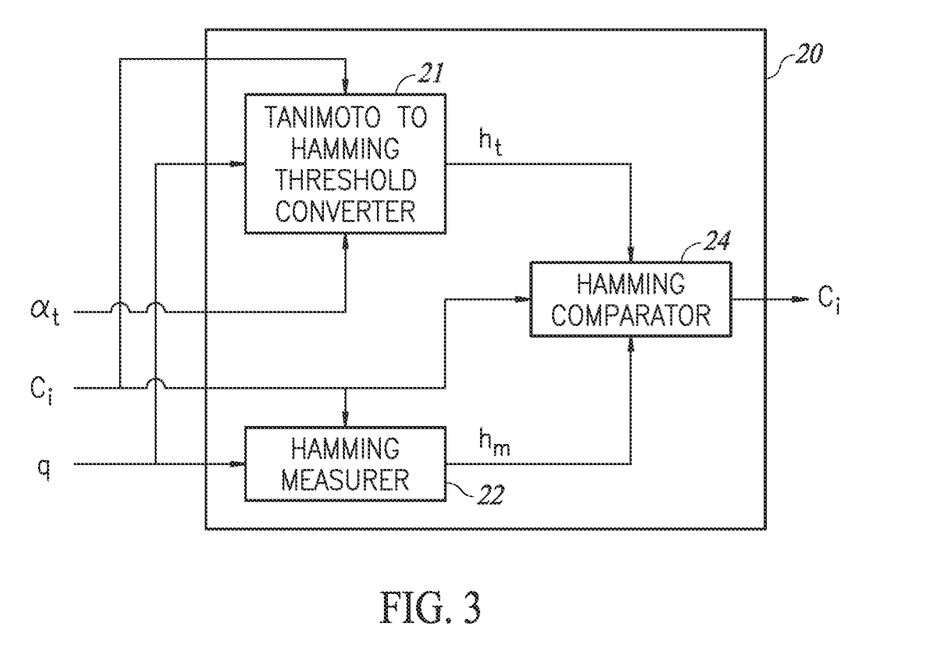
FIG. 3 is a schematic illustration of a preferred embodiment of a Hamming-Tanimoto measurement system.

Reference is now made to FIG. 3 which is an illustration of a preferred embodiment of a Hamming-Tanimoto measurement system 20 comprising a Tanimoto to Hamming threshold converter 21, a Hamming measurer 22 and a Hamming comparator 24. In this embodiment, Hamming-Tanimoto measurement system 20 calculates whether a candidate vector C is similar to a query vector q, as defined by Tanimoto threshold value $\alpha_t$.

Tanimoto to Hamming threshold converter 21 converts Tanimoto threshold $\alpha_t$ into Hamming threshold $h_t$. Hamming measurer 22 measures the Hamming distance $h_m$ between query vector q and candidate vector C and Hamming comparator 24 selects only those candidate vectors C that have a measured Hamming distance $h_m$ to query vector q that is less than or equal to the Hamming threshold $h_t$.

Figure 4:
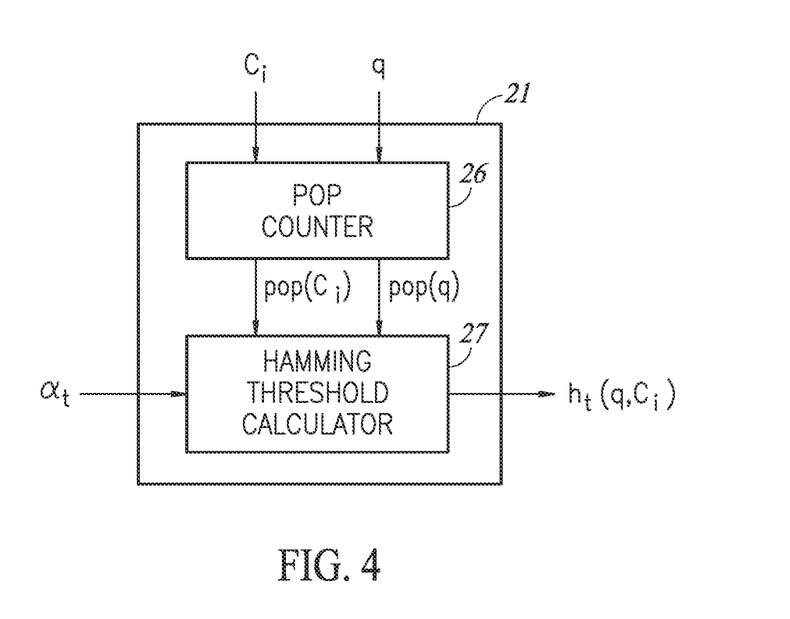
FIG. 4 is a schematic illustration of the elements of a Tanimoto to Hamming threshold converter useful in the system of FIG. 3.

Reference is now made to FIG. 4, which illustrates the elements of Tanimoto to Hamming threshold converter 21. Converter 21 comprises a pop counter 26 and a Hamming threshold calculator 27. Pop counter 26 calculates the pop counts of query vector q and of candidate vector C pop(q) and pop(C) respectively. Hamming threshold calculator 27 calculates $h_t(q, C)$ according to equation 4.

Figure 5:
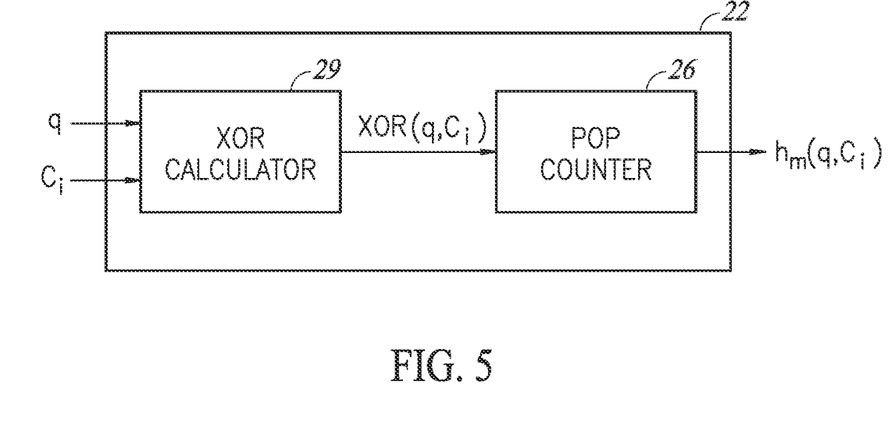
FIG. 5 is a schematic illustration of the elements of a Hamming measurer.

Reference is now made to FIG. 5 which illustrates the elements of Hamming measurer 22 to implement equation 2. Measurer 22 comprises another pop counter 26 and an XOR calculator 29. XOR calculator 29 outputs the XOR of query vector q and candidate vector C to pop counter 26. Pop counter 26 outputs the pop count of the XOR of query vector q and candidate vector C which is equal to the Hamming distance $h_m$ between query vector q and candidate vector C.

Returning to FIG. 3, Hamming comparator 24 then selects only those candidate vectors C that have a measured Hamming distance $h_m(q, C)$ less than or equal to Hamming threshold $h_t(q, C)$.

Applicant has realized that Hamming threshold $h_t$ is a function of pop(q) and pop(C) and that pop(q) is constant, but pop(C) may vary. Accordingly, system 5 may recalculate a new $h_t$ value for every successive pair of query and candidate vectors. This is computationally expensive.

Applicant has further realized that by grouping together all candidate vectors C which have the same pop count into a chunk D, each chunk Dj can be considered to have a pop count pop(Dj) which is the pop count of all the candidate vectors $C_i$ contained in chunk Dj. Hamming threshold calculator 27 may only need to calculate one Hamming threshold $h_t(q,Dj)$ for each pair of query vector q and chunk Dj according to equation 4.

Applicant has further realized that chunking candidate vectors may speed up similarity searches using Tanimoto metric, by allowing entire chunks of candidate vectors to be rejected prior to measurement.

Figure 6A:
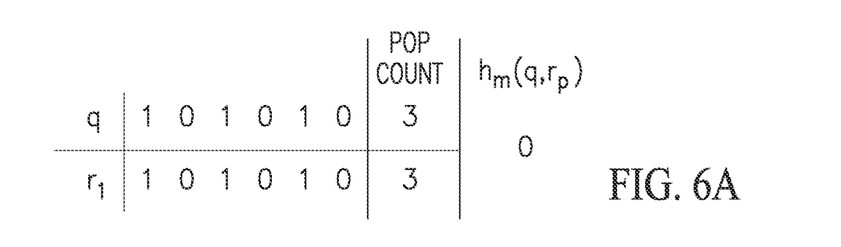
FIGS. 6A, 6B and 6C are pictorial illustrations of binary vectors.
Figure 6B:
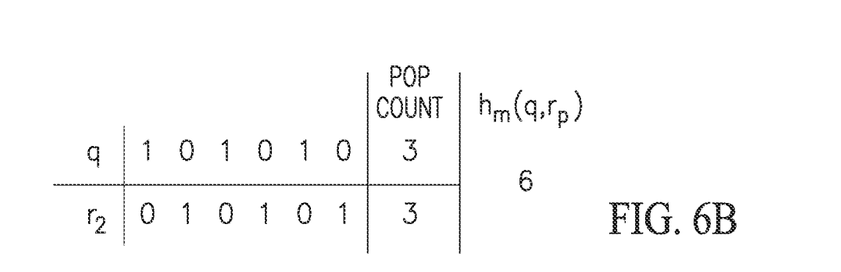

It will be appreciated that the smallest Hamming distance $h_m$ between any two binary vectors will be when all corresponding bit positions contain similar symbols or bits. Reference is now made to FIG. 6A which illustrates identical vectors, vector q and vector $r_1$. In this example, query vector q and candidate vector $r_1$ are identical and hence have a Hamming distance $h_m(q,r_1)$ of zero. It will be appreciated that a zero value of Hamming distance $h_m(q,r_1)$ can only occur when pop(q) is equal to pop($r_1$), however, equal pop(q) and pop($r_1$) do not guarantee a minimum Hamming distance $h_m$. Reference is now made to FIG. 6B which illustrates two vectors, a vector q and a vector $r_2$. Since vector q and vector $r_2$ have no similar symbols in corresponding bit positions, Hamming distance $h_m(q, r_2)$ is a maximum. In this case, since the vectors are 6-bit vectors, $h_m$ is 6.

Figure 6C:
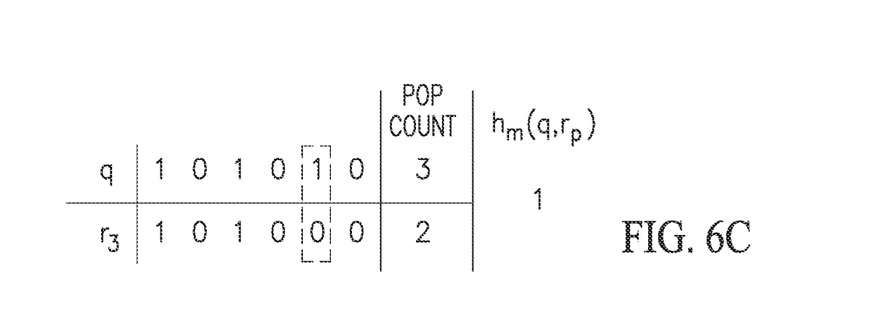

It will be appreciated that to have a Hamming distance $h_m$ of 0, then if there is a symbol in any bit position of vector q, then there will be a similar symbol in corresponding bit positions in vector C. So, for Hamming distance $h_m$ to be 0, there must be the same number of 1 s in vectors q and C, in other words, they have an equal pop count. This is the case in FIG. 6A. However, in FIG. 6C, vector q has a pop count of 3 and vector $r_3$ has a pop count of 2 In this example, there will always be at least one bit position in vector q that contains a 1 that contains a 0 in the corresponding bit position in vector $r_3$. So Hamming distance $h_m(q,r_3)$ cannot be lower than 1.

The lowest Hamming distance $h_m$ between vector q and vector $r_3$ can be expressed as:

$$h_{min}(q,r_3) = |\text{pop}(q) - \text{pop}(r_3)| \quad (5)$$

Accordingly, if the difference between pop(q) and pop (Dj) is greater than the defined Hamming threshold $h_t$, then none of the candidate vectors $C_i$ in chunk Dj can possibly be similar to query vector q and therefore, chunk Dj can be rejected apriori.

Figure 7:
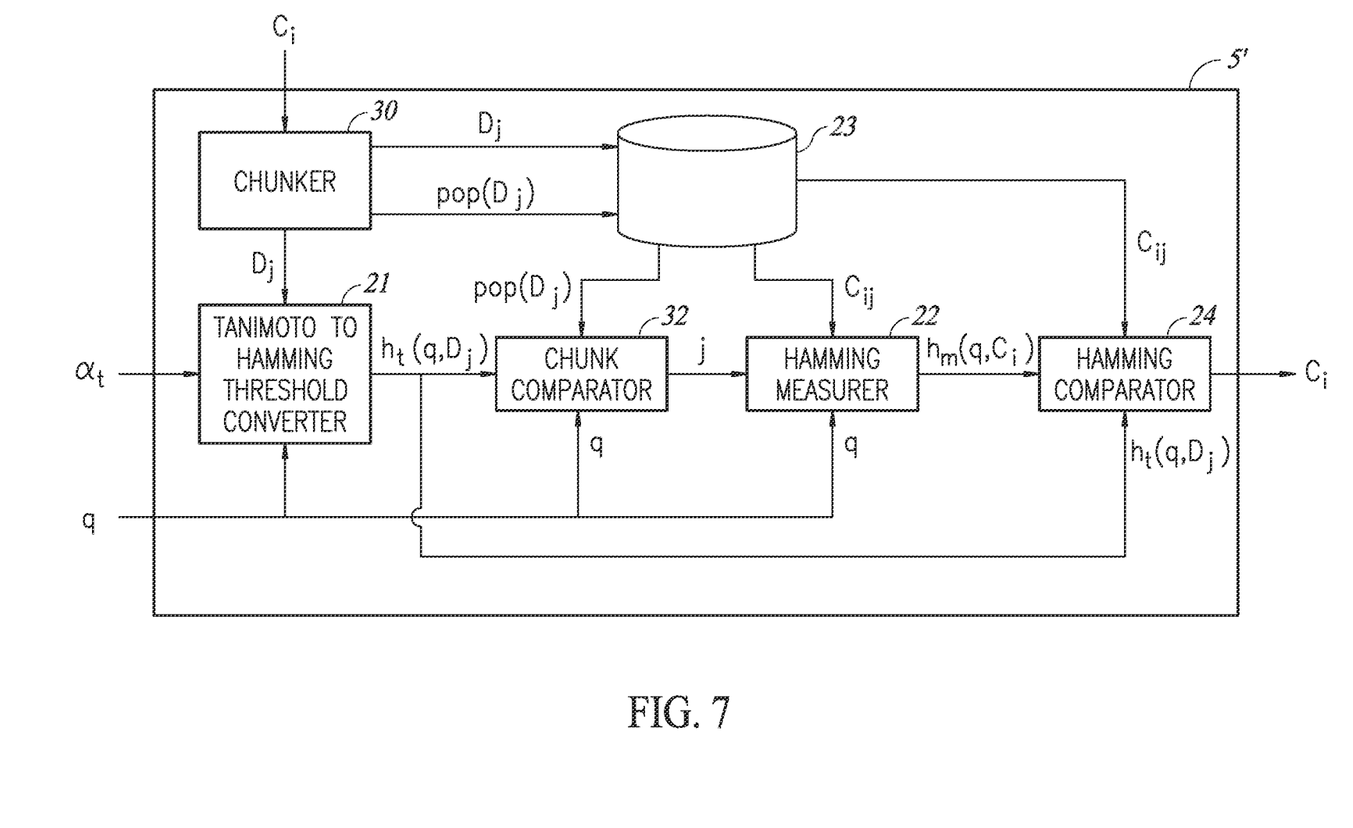
FIG. 7 is a schematic illustration of an alternative preferred embodiment of Tanimoto measurement system.

Reference is now made to FIG. 7 which illustrates a specific embodiment of the system, here labeled 5', which implements chunking of candidate vectors C. System 5' comprises a chunker 30, a chunk comparator 32, and a chunk and cluster repository 23, in addition to Tanimoto to Hamming threshold converter 21, Hamming measurer 22 and Hamming comparator 24 of system 5.

Chunker 30 may group all candidate vectors C into homogeneous pop count chunks D. Tanimoto to Hamming threshold converter 21 may convert Tanimoto threshold $\alpha_t$ to Hamming threshold $h_t$ for each pair of candidate vector q and chunk Dj. Using equation 5, chunk comparator 32 may select only chunks Dj which may possibly contain candidate vectors $C_i$. For the chunks Dj selected by chunk comparator 32, Hamming measurer 22 may measure the Hamming distance $h_m$ between each candidate vector $C_i$ in the current chunk Dj and query vector q as above. Hamming comparator 24 may select only those candidate vectors $C_i$ that have a measured Hamming distance $h_m$ to query vector q that is less than or equal to the Hamming threshold $h_t$. This process is repeated for all chunks Dj and all vectors $C_i$ within each chunk Dj.

Figure 8:
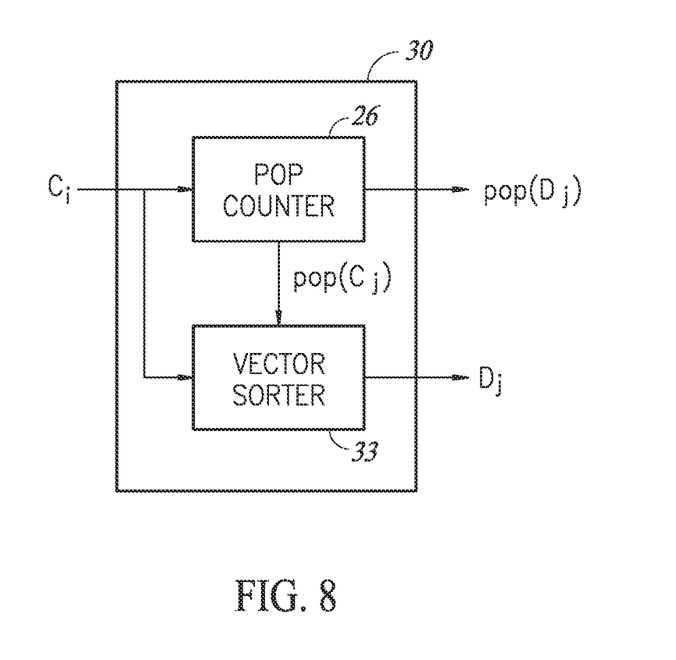
FIG. 8 is a schematic illustration of the elements of a chunker useful in the system of FIG. 7.

Reference is now made to FIG. 8, which illustrates the elements of chunker 30. Chunker 30 comprises another pop counter 26 and a vector sorter 33. For chunker 30, pop counter 26 may calculate the pop count pop($C_i$) of each candidate vector $C_i$ and vector sorter 33 may sort candidate vectors $C_i$ into chunks Dj. Chunks Di and pop(Di) may be stored in chunk and cluster repository 23 as illustrated in FIG. 7.

Figure 9:
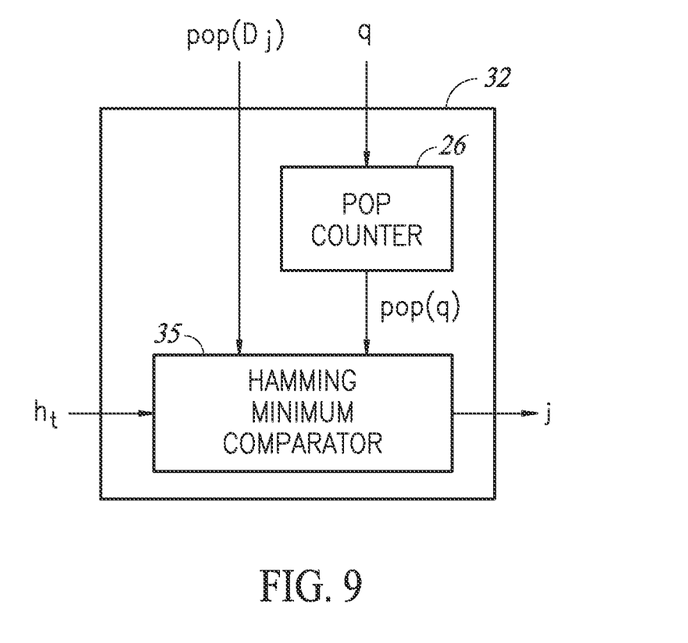
FIG. 9 is an illustration of the elements of a chunk comparator useful in the system of FIG. 7.

Reference is now made to FIG. 9, which illustrates the elements of chunk comparator 32 comprising another pop counter 26 and a Hamming minimum comparator 35. As discussed above, if the difference between pop(q) and pop (Dj) is less than or equal to $h_t$, then chunk Dj might contain candidate vectors $C_i$ that are similar to query vector q. Hamming minimum comparator 35 may select only those current chunks Dj that have a pop(q,$D_j$) that is less than or equal to Hamming threshold $h_t$.

It will be appreciated that by grouping candidate vectors C with homogeneous pop count into chunks D, search speed will increase. This is due to the elimination of repeated Hamming threshold $h_m$ calculations for vectors pairs that have identical pop(q) and pop($C_i$) as well as eliminating the measurement of chunks D that cannot possibly contain candidate vectors C that are similar to query vector q.

Applicant has realized that of the candidate vectors C in chunks D that chunk comparator 32 may have selected for measurement, only some, but not all candidate vectors C will be similar to query vector q. Applicant has realized that clustering candidate vectors C within chunks D may further reduce the number of candidate vectors to be measured and hence may further reduce processing time for searches.

Figure 10A:
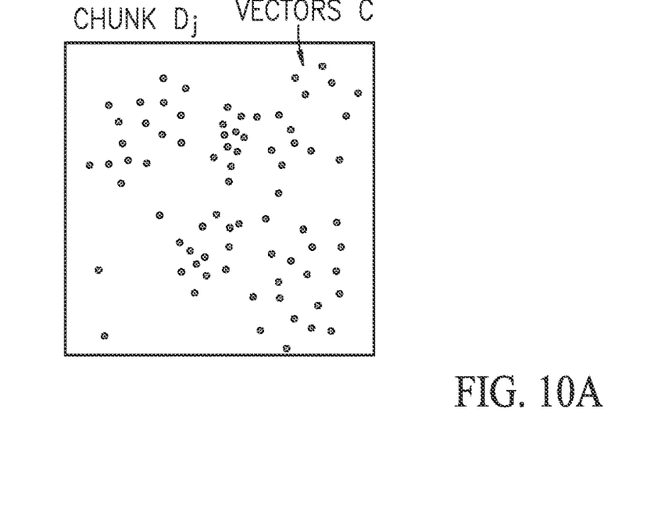
FIGS. 10A, 10B and 10C are pictorial illustrations of clustering binary vectors.
Figure 10B:
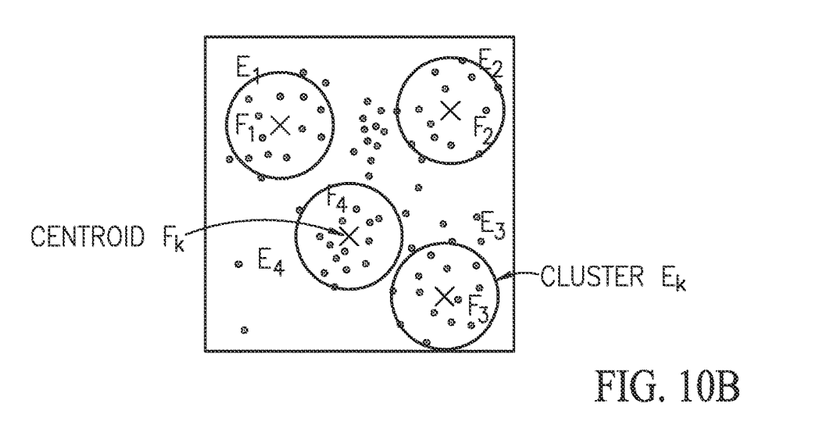
Figure 10C:
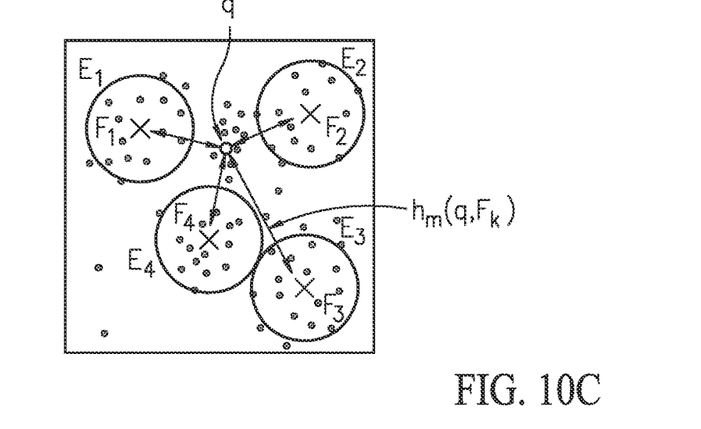

Reference is now made to FIGS. 10A, 10B and 10C which illustrate the steps in clustering candidate vectors C within chunks D. FIG. 10A illustrates a chunk Dj which has candidate vectors C, marked as dots within the two-dimensional space of Dj. As can be seen, candidates C are spread throughout the space; however, they are not evenly spread throughout the space.

Given that candidates C seem to be clustered within the space of FIG. 10A, candidate vectors C may be clustered into clusters E using a clustering algorithm, such as K-means or KNN (K nearest neighbor). The clustering algorithm may group those candidates C within chunk Dj that are reasonably close to a mean or centroid $F_k$ for each cluster $E_k$. As shown in FIG. 10B, there may be multiple clusters $E_k$, depending on the clustering algorithm and how its values are set. Each centroid $F_k$ may represent its cluster $E_k$ and may have a representative binary vector value that is a prototype of the candidates C within cluster $E_k$.

FIG. 10C illustrates how centroids F may be utilized to determine which clusters E may be rejected. FIG. 10C shows arrows from query vector q to each centroid $F_k$. The arrows represent Hamming distance $h_m(q,F_k)$ per centroid $F_k$. Note that some of the clusters E are relatively close to query q while one cluster, labeled $E_3$, is much further away.

If Hamming distance $h_m(q,F_k)$ is greater than $h_t$, then the entire cluster $E_k$ may be rejected, as the large Hamming distance $h_m(q,F_k)$ indicates that the entire cluster cannot contain candidate vectors $C_i$ that are similar to query vector q. To ensure that this is true, the clustering algorithm may require tight clustering, such that only those candidates C that are very close to one of the centroids $F_k$ may be included in cluster $E_k$.

Figure 11:
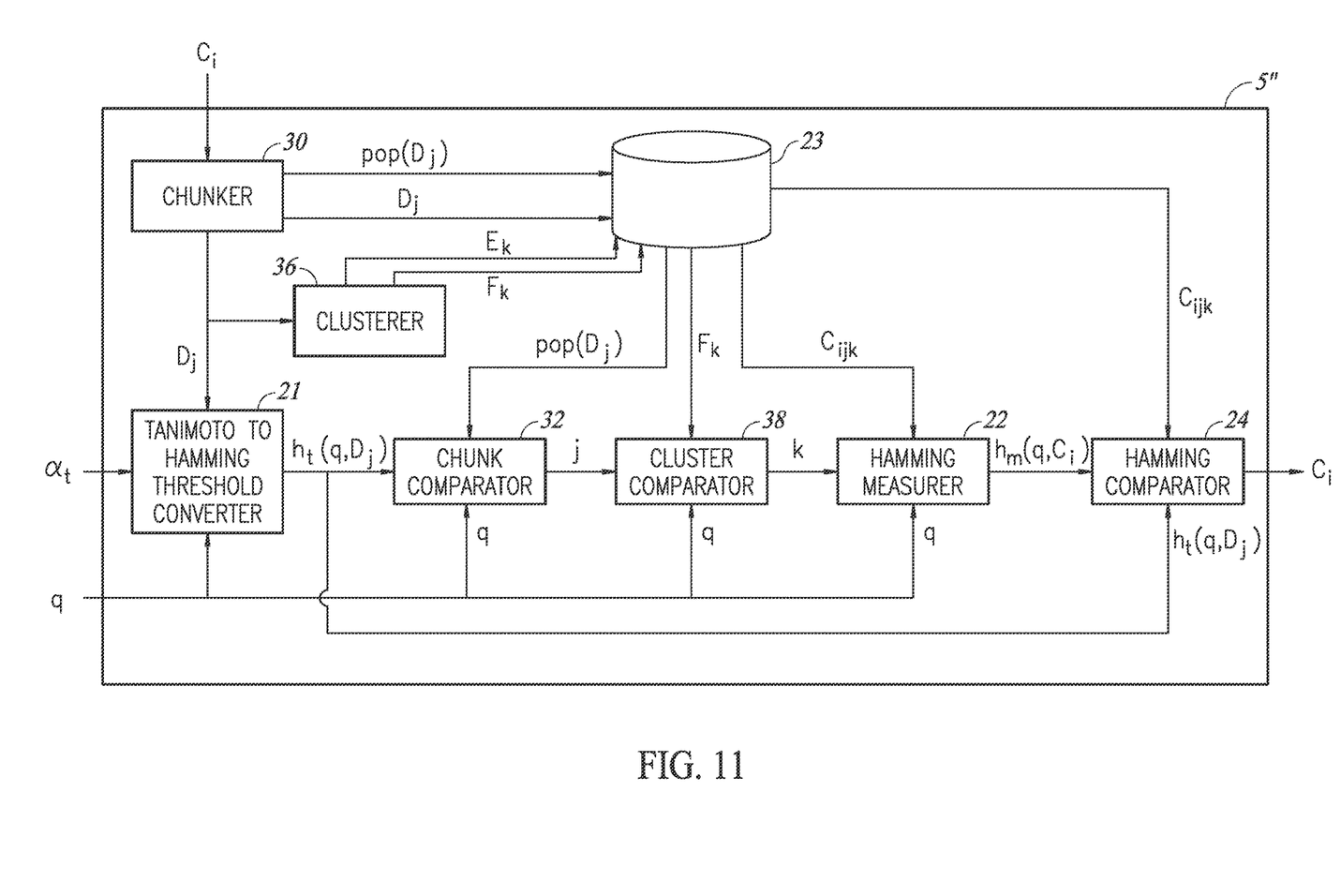
FIG. 11 is a schematic illustration of an alternative preferred embodiment of Tanimoto measurement system.

Reference is now made to FIG. 11, which illustrates a specific embodiment of the system, here labeled 5", which implements clustering of candidate vectors C. System 5" comprises a clusterer 36 and a cluster comparator 38 in addition to chunker 30, Tanimoto to Hamming threshold converter 21, chunk comparator 32, Hamming measurer 22, Hamming comparator 24 and chunk and cluster repository 23. As before, chunker 30 may sort all candidate vectors $C_i$ into homogeneous pop count chunks Dj. Clusterer 36 may group candidate vectors $C_i$ within chunks Dj into clusters $E_k$ using a clustering algorithm as described hereinabove. Tanimoto to Hamming threshold converter 21 may convert Tanimoto threshold $\alpha_t$ to the appropriate Hamming threshold $h_t$ for each chunk Dj.

As in the previous embodiment, chunk comparator 32 may calculate whether each chunk Dj may possibly contain useful candidate vectors $C_i$ and may output index value j of the selected chunks Dj. Cluster comparator 38 may review the selected chunks Dj and may select those clusters $E_k$ that may possibly contain useful candidate vectors $C_i$. Cluster comparator 38 may output the indices k of the selected clusters $E_k$. Hamming measurer 22 and Hamming comparator 24 may now operate on the reduced set of candidate vectors $C_i$, measuring the Hamming distance $h_m$ between each candidate vector $C_i$ in the selected clusters $E_k$ and query vector q and comparing Hamming measurement $h_m$ to Hamming threshold $h_t$ for the candidate vector $C_i$ as described previously. This process is repeated for all selected clusters $E_k$.

Figure 12:
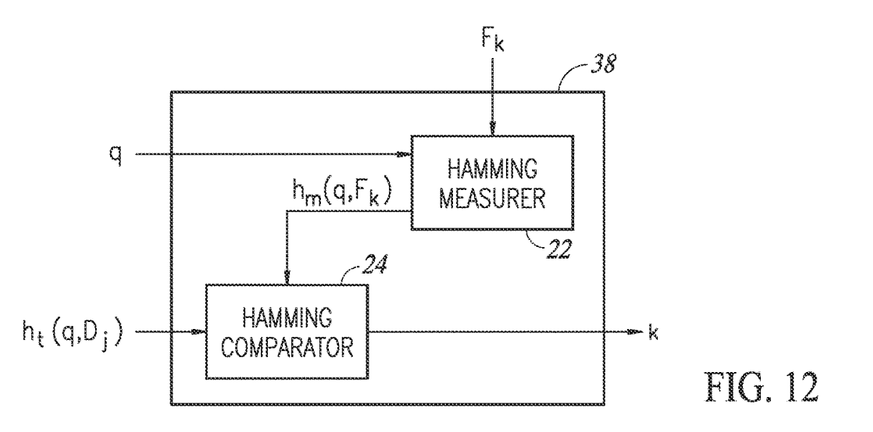
FIG. 12 is a schematic illustration of the elements of a cluster comparator useful in the system of FIG. 11.

Reference is now made to FIG. 12, which illustrates the elements of cluster comparator 38 comprising another Hamming measurer 22 and another Hamming comparator 24. Hamming measurer 22 may measure the Hamming distance $h_m(q,F_k)$ between query vector q and each cluster centroid $F_k$. Hamming comparator 24 may compare $h_m(q,F_k)$ with $h_t(q,D_j)$ and, if $h_m(q,F_k)$ less than or equal to $h_t(q,D_j)$, then Hamming comparator 24 may output cluster index k.

It will be appreciated that by excluding clusters $E_k$ whose centroid $F_k$ is not similar to query vector q, then search speed will further increase, since the number of candidate vectors being measured is further reduced.

The embodiments described hereinabove may be implemented on any suitable computing device.

Applicant has realized that Boolean functions are simple to implement on associative memory arrays in associative processing units (APUs), and can be performed in relatively few memory cycles. Furthermore, Boolean functions can be performed in parallel across a plurality (32k, 64k 128k . . . ) of binary vectors stored in associative memory array columns. Together, Boolean functions and massively parallel processing implemented on associative memory may provide orders of magnitude improvement in processing time and a significant reduction in computational complexity.

Figure 13:
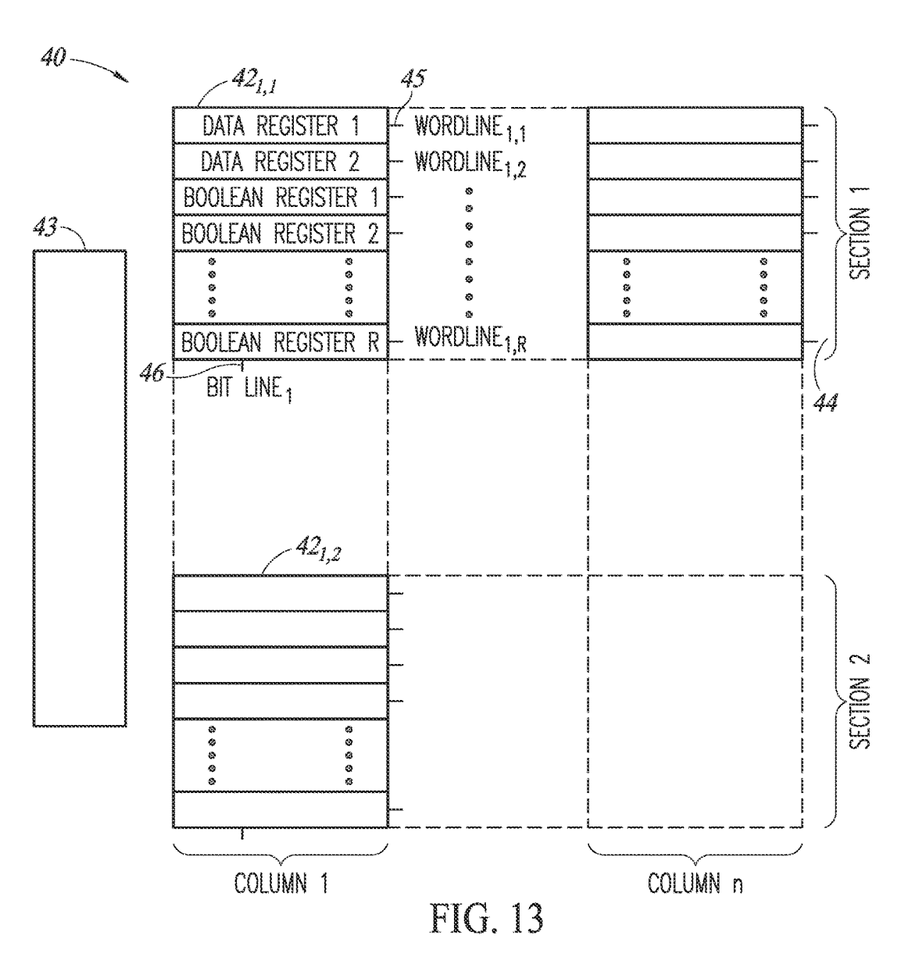
FIG. 13 is a schematic illustration of an associative memory array useful in the systems of FIGS. 3, 7 and 11.

Reference is now made to FIG. 13 which illustrates an associative memory array 40 comprising a plurality of bit line processors 42, and a controller 43 acting on memory array 40. Bit line processors 42 may be arranged in columns and rows in array 40, where each column of bit line processors 42 may operate on a single candidate vector $C_i$ from among a large plurality of candidate vectors $C_i$ and wherein each row of bit line processors 42 may operate on the same bit of each candidate vector $C_i$. Each bit line processor 42 may occupy a section 44 of memory that may have R rows, each row containing a 1-bit register. Each register in a bit line processor may have differing functions: registers 1 and 2 may be data registers storing a single bit of the data to be operated on, such as candidate vector $C_i$ or query vector q, and registers 3 thru R may be Boolean registers used for Boolean functions and calculations. So for example, bits 1 of candidate vector $C_1$ and query vector q may be stored in registers 1 and 2 respectively, of bit line processor #$42_{1,1}$ in column 1; bits 2 may be stored in registers 1 and 2 of bit line processor #$42_{1,1}$ in column 1, etc.

Each 1-bit register (in each row) of each bit line processor 42 may be connected to the corresponding register in all rows by a word line 45. Word line 45 is connected to controller 43. Controller 43 may activate all corresponding registers in a row simultaneously. This is the basis for massive parallel processing on associative memory array 40.

In addition, the registers in each bit line processor 42 are connected vertically together via a bit line 46. Using the combination of word lines 45 and bit lines 46, controller 43 may activate a single register, or multiple registers simultaneously. When performing an operation between candidate vector Ci and query q, controller 43 may simultaneously activate all rows where each vector is stored, thereby to perform the same function on all bits of the vectors at one time, each operation within its bit line processor. By activating multiple bit lines 46, multiple bits may be operated on in parallel.

The associative processing unit APU (not illustrated) that comprises both bit line processors 42 and controller 43 may perform Boolean functions. For example, on memory cycle 1, controller 43 may activate the rows of register 1 (storing candidate vector Ci). This will cause bit lines 46 to receive the data of register 1. On cycle 2, controller 43 may activate the rows of register 5 to receive the data on bit lines 46. On cycle 3, controller 43 may repeat the process with register 2 (storing query vector q) and may activate register 5 to receive the data on bit lines 46 only if the data to be written is different than that which is already stored therein. This creates a Boolean XOR between the content from register 1 and the content from register 2. Controller 43 can perform this in parallel on all bits of the vector stored in the column, but also on all parallel columns by manipulating word lines 45 and bit lines 46.

It will be appreciated that by storing a plurality of vectors in parallel columns, calculations and Boolean functions may be performed fast and on a plurality of vectors.

Applicant has realized that the embodiments of FIGS. 3, 7 and 11 may be implemented in associative memory such as described with respect to FIG. 13 and that, due to the massively parallel processing of the APU of FIG. 13, similarity search time may be increased by many orders of magnitude.

Figure 14A:
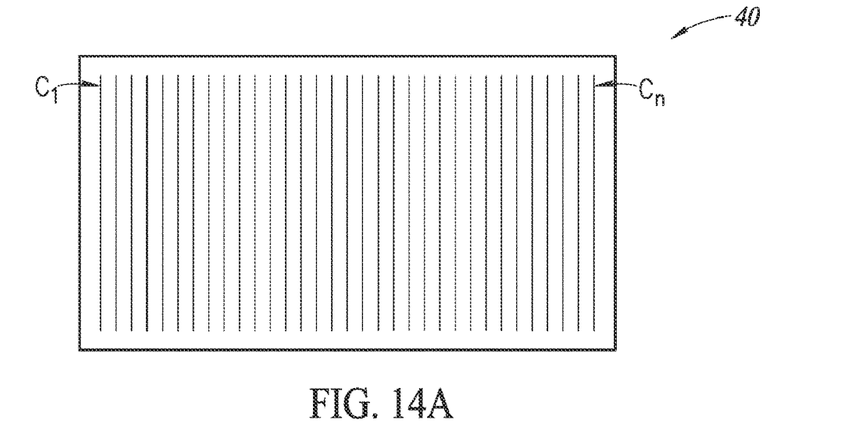
FIG. 14A is a pictorial illustration of unsorted vectors in an associative memory array useful in the systems of FIGS. 3, 7 and 11.
Figure 14B:
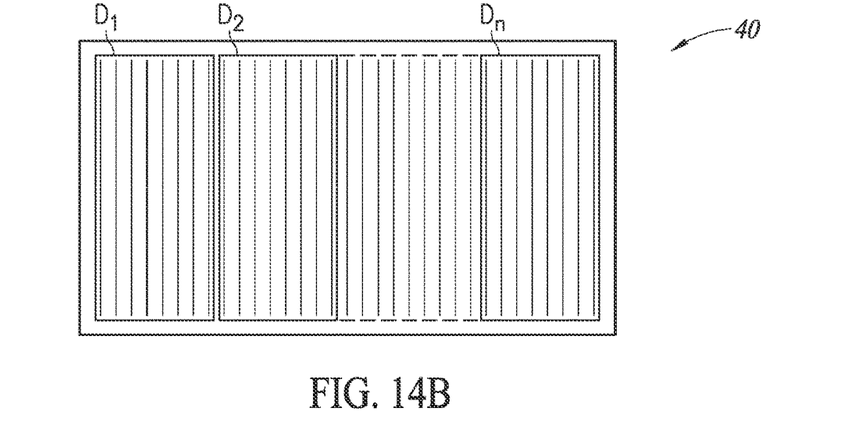
FIG. 14B is a pictorial illustration of chunked vectors in an associative memory array useful in the systems of FIGS. 7 and 11.
Figure 14C:
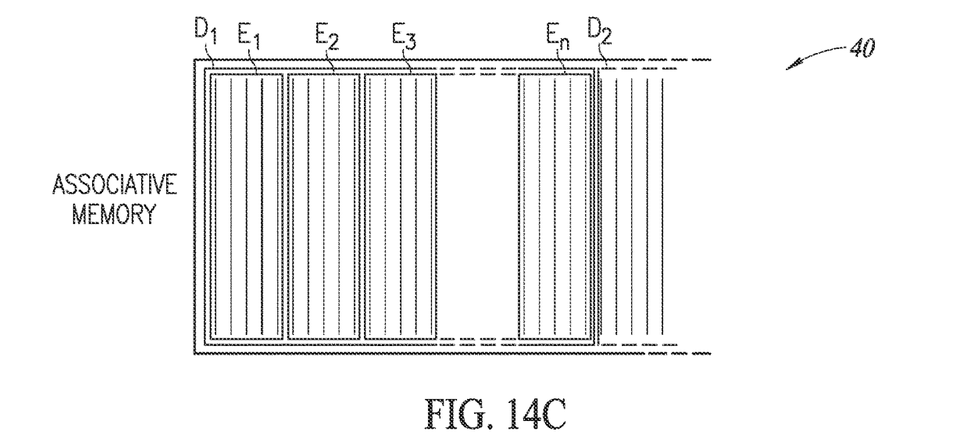
FIG. 14C is a pictorial illustration of chunked and clustered vectors in an associative memory array useful in the system of FIG. 11.

Reference is now made to FIGS. 14A, 14B and 14C that illustrate candidate binary vectors C stored in parallel columns of associative memory 40. In the embodiment of FIG. 3, Hamming distance h was measured between candidate vectors C and query vector q. FIG. 14A illustrates the candidate vectors C stored in columns of associative memory. The controller and individual rows and bit line processors are not illustrated, but in this example, each bit of a candidate vector C is stored in register 1 of each bit line processor as described above. The controller will activate all bits of the candidate vector C at the same time, and also perform all calculations and manipulations in parallel on the plurality of candidate vectors C and query vector q.

In the embodiment of FIG. 7, candidate vectors C with the same pop count were grouped into chunks D. Each chunk was then stored in a section of memory. FIG. 14B illustrates how the candidate vectors are still stored in parallel columns in associative memory, but organized in chunks D. By manipulating word lines and bit lines, the controller can perform massively parallel processing on chunks D. As mentioned previously, this reduces the number of Hamming threshold calculations that need to be performed as well as allowing entire chunks of candidate vectors to be discounted.

In the embodiment of FIG. 11, candidate vectors in the chunks were grouped into clusters E each with a centroid F. FIG. 14C illustrates the clusters E of candidate vectors C within chunks D. Again, by manipulating word lines and bit lines, controller 43 may operate on individual clusters E to increase search speed.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A system for measuring similarity between a binary query vector and a plurality of binary candidate vectors, the system comprising:
   a pop counter to generate pop counts of said binary candidate vectors, wherein each pop count is a number of occurrences of a selected symbol in at least one of said binary candidate vectors;
   a chunker to group said binary candidate vectors according to their pop counts into chunks;
   a clusterer to use a K-means algorithm to generate clusters of said chunks, each cluster having a centroid; and
   a cluster comparator to select at least one of said clusters whose centroid is similar to said binary query vector and to perform Tanimoto calculations in terms of Hamming distances using Boolean operations between said binary candidate vectors of said cluster and said binary query vector.

2. The system of claim 1 wherein said cluster comparator comprises:
   a Hamming measurer to measure a Hamming distance between said binary query vector and said centroid; and
   a Hamming comparator to select only said clusters whose centroid is within a Hamming measurement threshold of said binary query vector and said at least one of said chunks.

3. The system of claim 1 and also comprising an associative memory array having columns storing vectors, at least one column for said binary query vector and at least one column for each one of said plurality of binary candidate vectors, wherein at least one of said chunks is stored in a section of said associative memory array.

4. The system of claim 3 wherein at least one said cluster is stored together within its said chunk.

5. A method for measuring similarity between a binary query vector and a plurality of binary candidate vectors, the method comprising:
   generating pop counts of said binary candidate vectors, wherein each pop count is a number of occurrences of a selected symbol in at least one of said binary candidate vectors;
   grouping said binary candidate vectors according to their pop counts into chunks;
   using a K-means algorithm to generate clusters of said chunks, each cluster having a centroid;
   selecting at least one of said clusters whose centroid is similar to said binary query vector; and
   performing Tanimoto calculations in terms of Hamming distances using Boolean operations between said binary candidate vectors of said cluster and said binary query vector.

6. The method of claim 5 wherein said selecting comprises:
   measuring a Hamming distance between said binary query vector and said centroid; and selecting only said clusters whose centroid is within a Hamming measurement threshold of said binary query vector and said at least one of said chunks.

7. The method of claim 5 and also comprising, in an associative memory array having columns storing vectors, at least one column for said binary query vector and at least one column for each one of said plurality of binary candidate vectors, storing at least one of said chunks in a section of said associative memory array.

8. The method of claim 7 wherein said storing comprises storing together at least one said cluster within its said chunk.

\* \* \* \* \*